(12) United States Patent
Lin et al.

(10) Patent No.: US 8,431,737 B2
(45) Date of Patent: Apr. 30, 2013

(54) DRYING AGENT

(71) Applicant: Chung Yuan Christian University, Tao-Yuan (TW)

(72) Inventors: Chia-Her Lin, Tao-Yuan (TW); Hsin-Kuan Liu, Tao-Yuan (TW); Tai-Hsing Tsao, Tao-Yuan (TW)

(73) Assignee: Chung Yuan Christian University, Tao-Yuan (TW)

( * ) Notice: Subject to any disclaimer, the term of this patent is extended or adjusted under 35 U.S.C. 154(b) by 0 days.

(21) Appl. No.: 13/659,098

(22) Filed: Oct. 24, 2012

(65) Prior Publication Data

US 2013/0066106 A1 Mar. 14, 2013

Related U.S. Application Data

(62) Division of application No. 12/777,906, filed on May 11, 2010, now Pat. No. 8,318,974.

(30) Foreign Application Priority Data

Mar. 2, 2010 (TW) .............................. 99105916 A

(51) Int. Cl.
*C07C 63/313* (2006.01)

(52) U.S. Cl.
USPC .......................................................... 562/480

(58) Field of Classification Search ........................ None
See application file for complete search history.

(56) References Cited

PUBLICATIONS

Liu et al. "Microwave synthesis and single-crystal-to-single-crystal transformation of magnesium coordination polymers exhibiting selective gas adsorption and luminescence properties" CrystEngComm, 2009, 11, 1462-1468.

Liu et al. "Direct-mixing assembly of a magnesium coordination complex as recyclable water adsorbent" CrystEngComm, 2010, 12, 1044-1047.

*Primary Examiner* — Yevegeny Valenrod

(74) *Attorney, Agent, or Firm* — Stout, Uxa, Buyan & Mullins, LLP

(57) ABSTRACT

One embodiment of the present invention discloses a drying agent having the formula: $[Mg_2(BTEC)(H_2O)m] \cdot nH_2O$, where m denotes zero or positive integer from 1 to 10, and n denotes zero or positive integer from 1 to 6. Another embodiment of the present invention provides a method for forming a drying agent.

6 Claims, 7 Drawing Sheets

DRYING AGENT

CROSS-REFERENCE TO RELATED APPLICATIONS

This application is a divisional of U.S. application Ser. No. 12/777,906, filed on May 11, 2010 and entitled DRYING AGENT AND METHOD FOR FORMING THE SAME, which claims priority to Taiwan Patent Application No. 099105916, filed on Mar. 2, 2010, the entire contents both of which are incorporated herein by reference.

BACKGROUND OF THE INVENTION

1. Field of the Invention

The present invention relates to a drying agent and its forming method conforming to the concepts of Green Chemistry.

2. Description of Related Art

Molecular organization through self-assembly processes involving spontaneous and reversible association of two or more components to generate a large complex and molecular architecture has been a focus of scientific attention in recent years. Conventional self-assembly processes in coordination chemistry are typically carried out in solution by employing diffusions between liquid phase and liquid phase, diffusions between liquid phase and gas phase, and hydrothermal syntheses. These methods typically consume a great deal of energy, and the solvent-reagent interactions may limit the types of materials that can be prepared through this route.

Nowadays, Green Chemistry encourages the design of products and processes that reduce or eliminate use and generation of hazardous substances. Green Chemistry includes 12 principles such as: (1) It is better to prevent waste than to treat or clean up waste after it is formed; (2) Synthetic methods should be designed to maximize the incorporation of all materials used in the process into the final product; (3) Wherever practicable, synthetic methodologies should be designed to use and generate substances that possess little or no toxicity to human health and the environment; (4) Chemical products should be designed to preserve efficacy of function while reducing toxicity; (5) The use of auxiliary substances, e.g., solvents, separation agents, and the likes, should be made unnecessary wherever possible and, innocuous when used; (6) Energy requirements should be recognized for their environmental and economic impacts and should be minimized. Synthetic methods should be conducted at ambient temperature and pressure; and so on.

To achieve the concepts of Green Chemistry, some new synthesis methods have been proposed. For example, the use of mechanochemical methods and liquid-assisted grinding in solid-state synthesis has attracted more research effort due to their advantages in easy process and less solvent preparation as well as high yields. An easier and more environments-friendly process, however, is still a purpose to be pursued in Green Chemistry. On the other hand, the performance of conventional drying agents such as silicon gels, molecular sieves, calcium oxide, and magnesium sulfate is limited; therefore a reusable, better drying agent is required to be applied in various fields.

Therefore, it would be advantageous to provide drying agents and their producing method that can meet the requirements of the Green Chemistry and reveal excellent properties.

SUMMARY OF THE INVENTION

An object of the present invention is to provide drying agents and their producing method that can meet the requirements of the Green Chemistry and reveal excellent properties.

According to the object, one embodiment of the present invention provides a drying agent with a formula $[Mg_2(BTEC)(H_2O)_m] \cdot nH_2O$, wherein m denotes zero or positive integer from 1 to 10, and n denotes zero or positive integer from 1 to 6.

According to the object, one embodiment of the present invention provides a method for producing drying agents. The method comprises to directly mixing 1,2,4,5-benzenete-tracarboxylic acid, magnesium hydroxide, and liquid water to proceed an acid-base reaction and thus obtain a drying agent with a formula $[Mg_2(BTEC)(H_2O)_{10}] \cdot nH_2O$, wherein n is positive integer from 1 to 6.

DETAILED DESCRIPTION OF THE PREFERRED EMBODIMENT

Reference will now be made in detail to specific embodiments of the invention. Examples of these embodiments are illustrated in accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a through understanding of the present invention. The present invention may be practiced without some or all of these specific details. In other instances, well-known process operations and components are not been described in detail in order not to unnecessarily obscure the present invention. While drawings are illustrated in details, it is appreciated that the quantity of the disclosed components may be greater or less than that disclosed, except expressly restricting the amount of the components.

A preferred embodiment of the present invention provides a producing method of drying agents with the following chemical reaction: $H_4(BTEC) + 2Mg(OH)_2 + 12H_2O \rightarrow [Mg_2(BTEC)(H_2O)_{10}] \cdot 6H_2O$.

In the preferred embodiment, the drying agent $[Mg_2(BTEC)(H_2O)_{10}]\cdot 6H_2O$ is obtained by directly mixing stoichiometric amount of 1,2,4,5-benzenete-tracarboxylic acid ($H_4BTEC$), magnesium hydroxide [$Mg(OH)_2$], and liquid water ($H_2O$). For example, in a specific embodiment, 0.685 g (2.7 mmole) of 1,2,4,5-benzenete-tracarboxylic acid, 0.315 g (5.4 mmole) of magnesium hydroxide, and 0.58 g (32.4 mmole) of water are placed into a container and directly mixed under room temperature and atmospheric pressure, i.e., ambient temperature and pressure. A proper agitation or other physical way may be used to assist the mixing of reactants for obtaining powder-shaped drying agent—$[Mg_2(BTEC)(H_2O)_{10}]\cdot 6H_2O$, which is referred to as "compound 1" hereinafter—in one or several embodiments after.

The above direct-mixing method is a solvent-free method and uses a quite small quantity of water and produces free of by-product and intermediate. Hence it is a solid-state reaction with a yield rate about 95% or more. A classical calorimetric method determines that the heat of formation of the above direct-mixing method is −54.2 kJ/mol by measuring the temperature change of an adiabatic water bat.

Figure 1:
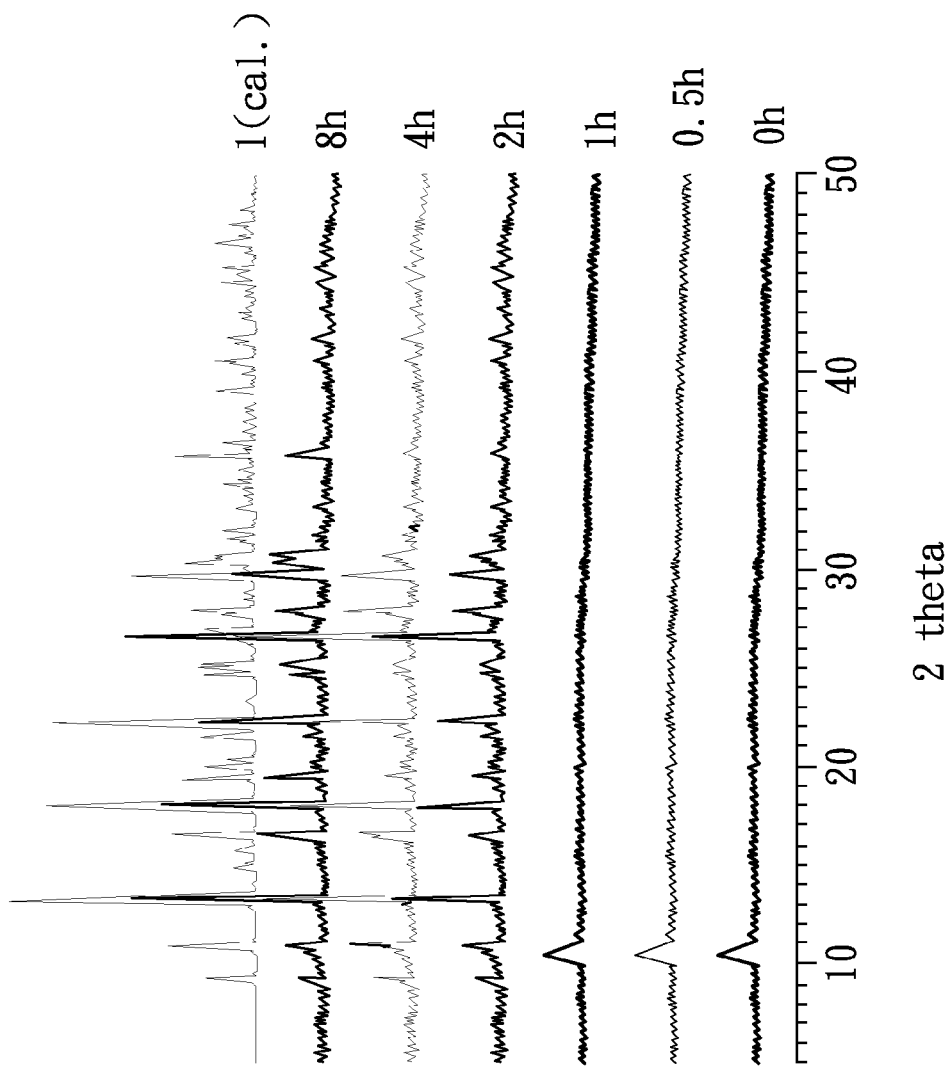
FIG. 1 shows a time develop of powder XRD patterns observed for a solid-state mixture of $Mg(OH)_2$ and $H_4BTEC$ (2:1) left in an atmospheric environment with a relative humidity (RH) about 70%.

In the preferred embodiment, the water needed for reaction is obtained by adding liquid water. In some embodiments of the present invention, however, the water needed for reaction may be gaseous. For example, the water may be obtained from air, or, from a humidified or o humidity-controlled environment. For example, FIG. 1 is time develop of powder X-ray diffraction (XRD) patterns observed for a solid state mixture of $Mg(OH)_2$ and $H_4BTEC$ (2:1) left in an atmospheric environment with a relative humidity (RH) about 70%, and "1(cal)" denotes the XRD pattern of the compound 1. As shown in FIG. 1, after 8 hours, the XRD pattern of the mixture is same as the compound 1. This means that $Mg(OH)_2$ and $H_4BTEC$ have absorbed water from air and form compound 1.

Figure 2:
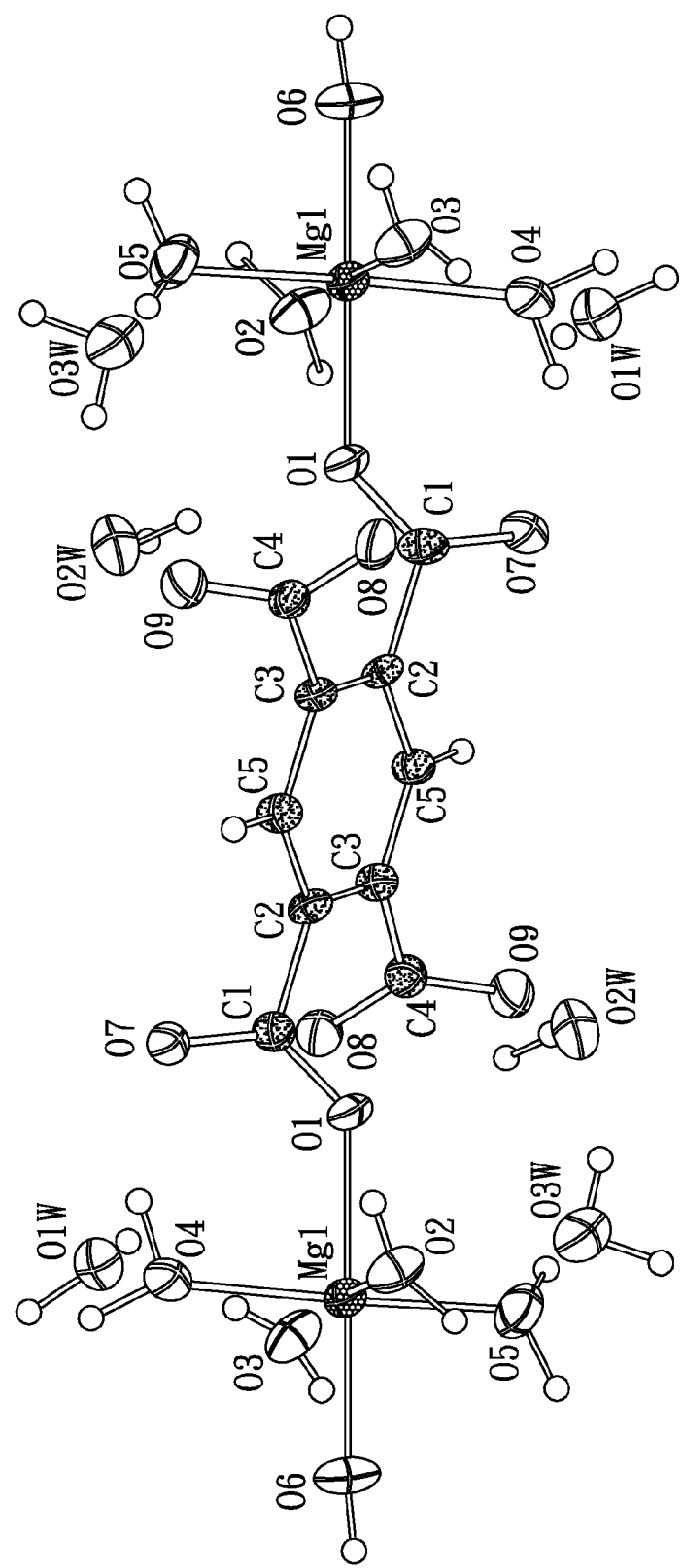
FIG. 2 shows the molecular structure of compound 1 $[Mg_2(BTEC)(H_2O)_{10}] \cdot 6H_2O$ produced by one embodiment of the present invention.

An acicular crystal of suitable size of compound 1 produced by the above-mentioned formula was selected for single-crystal structure analysis, and the chemical formula was determined as $[Mg_2(BTEC)(H_2O)_{10}]\cdot 6H_2O$, with a molecular structure as shown in FIG. 2. The basic motif of compound 1 is composed of one $BTEC^{4-}$ anion, to which two divalent magnesium cations are connected through the carboxyl groups in a para-position with respect to each other. The other two carboxyl groups are free. Each magnesium atom is connected to BTEC anion through one O1 atom with the typical Mg—O bond, with bond length of 2.104 Å(Mg(1)-O(1)). The BTEC anion is therefore coordinated in a bis-monodentate fashion and forms a $\mu_2$-bridge between two magnesium atoms. In addition, both magnesium atoms are six-coordinated, and the remaining five coordination positions in the $MgO_6$ octahedron are accomplished by oxygen atoms of water molecules in terminal positions with Mg—O bond length from 2.017(3) Å to 2.163(2) Å. Thus, the formula of this molecule can be written as $(H_2O)_5Mg(\mu-C_6H_2(COO)_4)Mg(H_2O)_5$.

The above-mentioned method produces compound 1 featuring in unique molecule packing, air stability, and facile preparation. In addition, highly favorable intra- and intermolecular hydrogen bonding in compound 1 between the carboxylate oxygen atoms and coordinated water molecules as well as between carboxylate oxygen atoms and lattice waters might strongly stabilize the structure.

Figure 3:
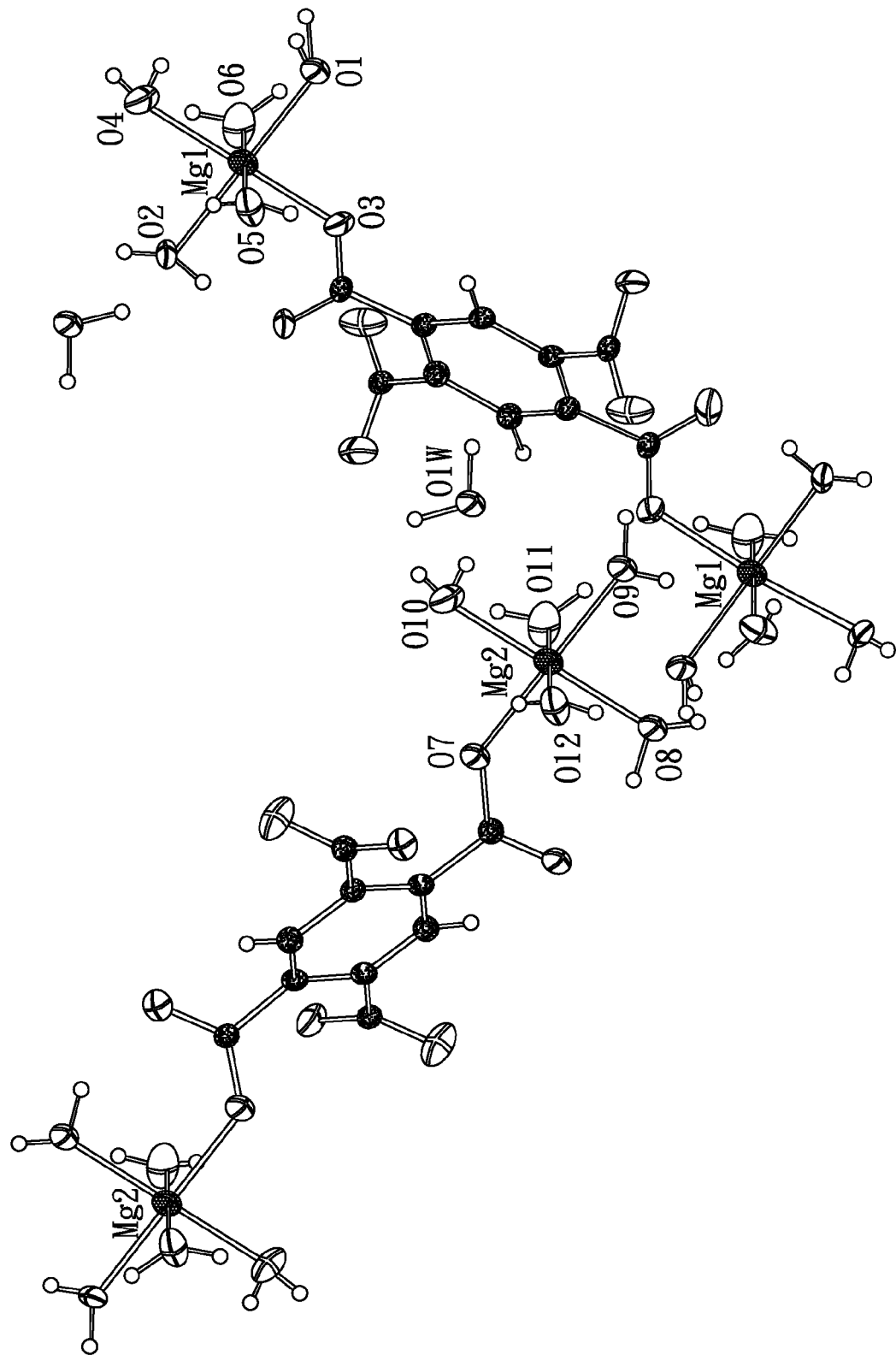
FIG. 3 shows the molecular structure of compound 2 $[Mg_2(BTEC)(H_2O)_{10}] \cdot H_2O$ produced by one embodiment of the present invention.

Compound 1 can be heated and dehydrated to form $[Mg_2(BTEC)(H_2O)_{10}]\cdot H_2O$, which is referred to as compound 2 hereinafter, and whose structure is shown in FIG. 3. The heating method is not limited but the heating temperatures are limited to below 500° C. For example, in a specific embodiment, compound 1 is placed in an oven controlled at 120° C. for a period of time to form compound 2. The crystal structure analysis revealed that compound 2 also contains di-nuclear magnesium with octahedral $MgO(H_2O)_5$ connected together with same carboxylate anion. Each magnesium atom is coordinated to six oxygen atoms. One of the oxygen atoms, from carboxylate groups, forms the typical Mg—O bond with a bond length of 2.081(2) Å for Mg(1)-O(3) and 2.091(2) Å for Mg(2)-O(7). The other five oxygen atoms, from water molecules in terminal position, form Mg—O bonds with bond lengths ranging from 2.039(2) Å to 2.163(2) Å. The organic BTEC anions in compound 2 are also fully deprotonated and adopt a $\mu^2$-linkage.

Figure 4:
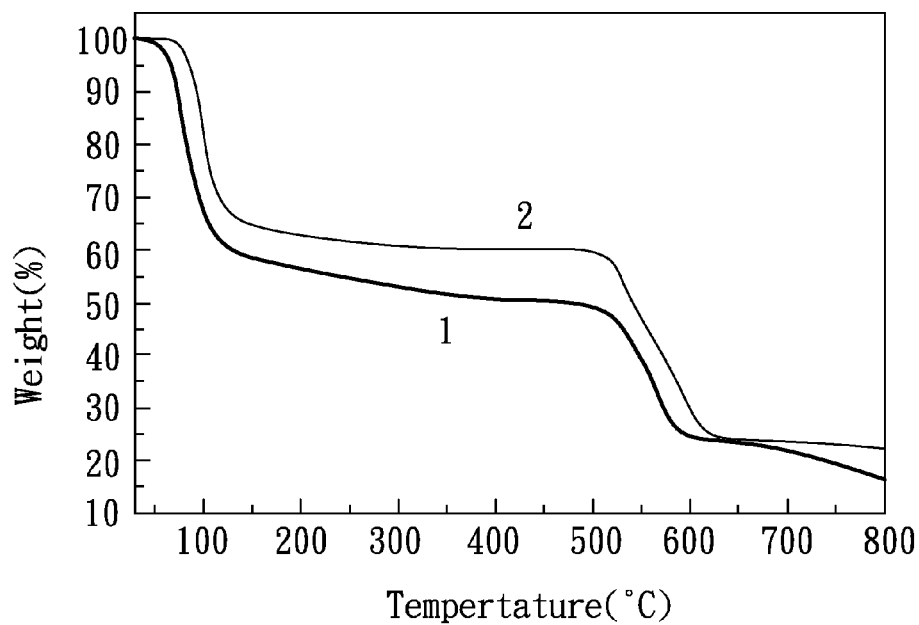
FIG. 4 shows a thermal gravimetric analysis (TGA) of compound 1 and compound 2 produced by an embodiment of the present invention.

FIG. 4 shows a thermal gravimetric analysis (TGA) of compound 1 and compound 2 produced by an embodiment of the present invention, in which it is observed a steep decrease in weight as the temperature was raised from 60 to 120° C., followed by a gradual weight loss up to 400° C. A total weight loss of 49.0% observed between 70 to 400° C. can be accounted for the release of six lattice and ten coordinated water molecules from compound 1. The complete dehydration transforms compound 1 into a poorly crystalline phase with a proposed formula, $[Mg_2(BTEC)]$, which is based on elemental analysis and denoted as M2B. M2B is thermally stable up to about 500° C. Compound 2 is thermally stable up to 70° C., and then, a steep weight loss of 39.2% is observed as the temperature is raised to 300° C. The weight loss observed between 70 to 300° C. corresponds to the removal of one lattice and ten coordinated water molecules (calculated 39.9%) from compound 2. The complete dehydration also converts compound 2 into a poorly crystalline phase of M2B, and similarly to compound 1, its organic part starts to decompose when heating temperature is above 500° C., and white MgO is formed after heating to 800° C.

Figure 5:
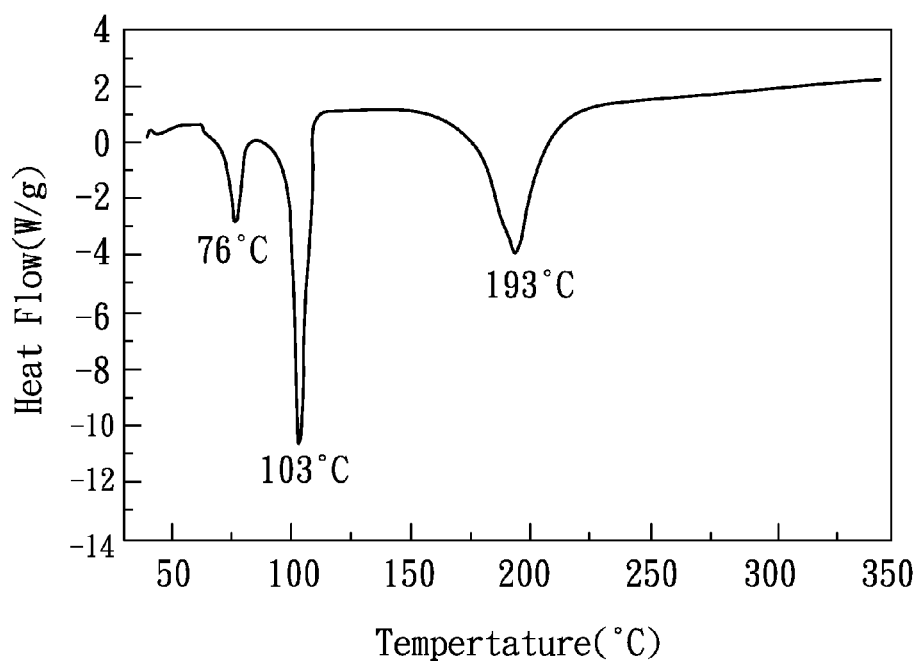
FIG. 5 shows a Differential Scanning Calorimetry (DSC) of compound 1 produced by an embodiment of the present invention.

FIG. 5 shows a Differential Scanning Calorimetry (DSC) of compound 1 produced by the embodiment of the present invention. The DSC analysis shows three endothermic peaks at 76, 103 and 193° C. Two peaks at 76 and 103° C. respectively indicate that compound 1 loses five of the six lattice water molecules and compound 2 is formed. The last endothermic peak indicates that further heating removes the last lattice water molecule and aqua ligands at 193° C.

Figure 6:
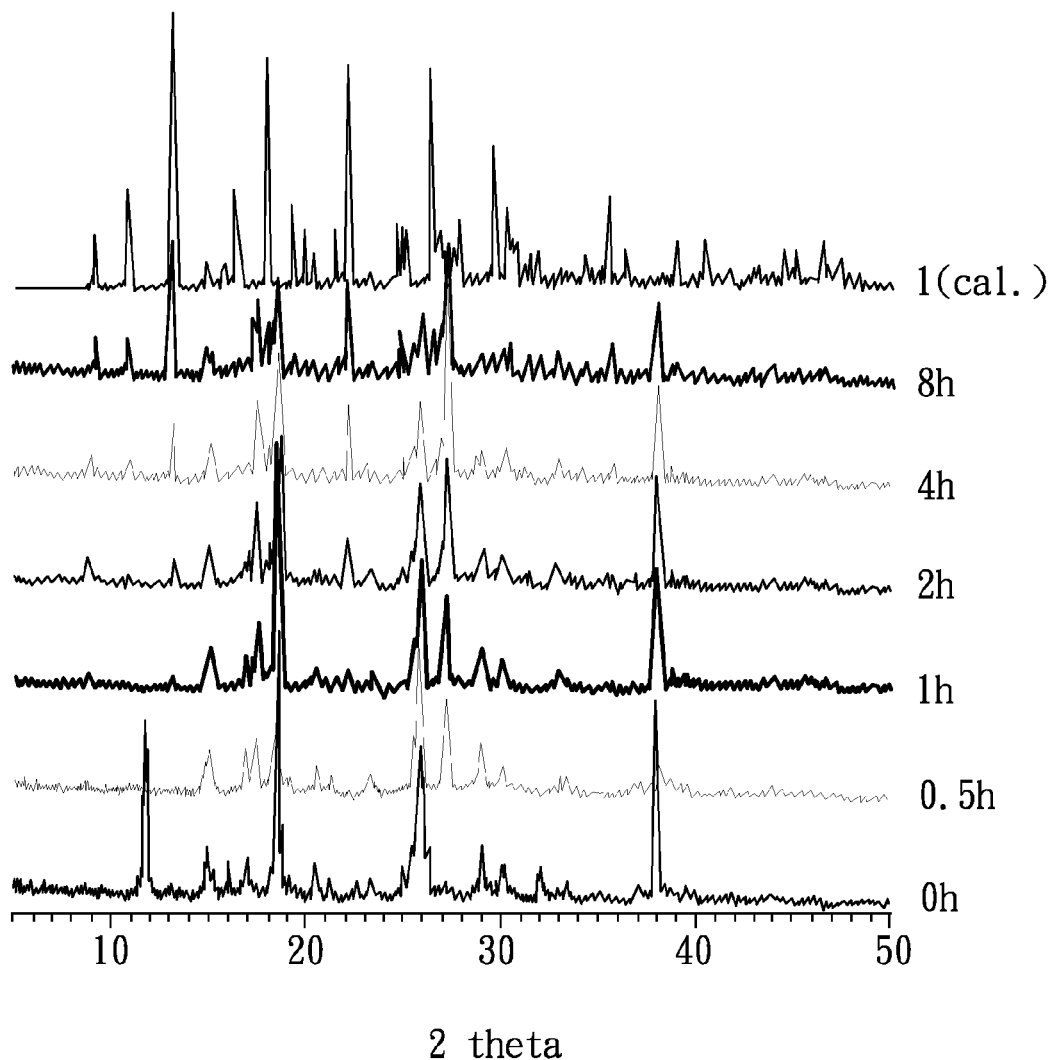
FIG. 6 shows an in situ powder XRD analysis of M2B under ambient conditions at 70% relative humidity (RH).

FIG. 6 shows an in situ powder XRD analysis of M2B under ambient conditions at 70% relative humidity (RH), wherein "1(cal.)"† denotes the XRD pattern of compound 1, and others are XRD patterns of M2B placed in various period of time. The analysis shows that M2B transforms to the crystalline compound 1 under the test conditions in 8 hrs, as indicated by the XRD patterns of the rehydrated material that match the calculated powder X-ray pattern of compound 1.

Figure 7:
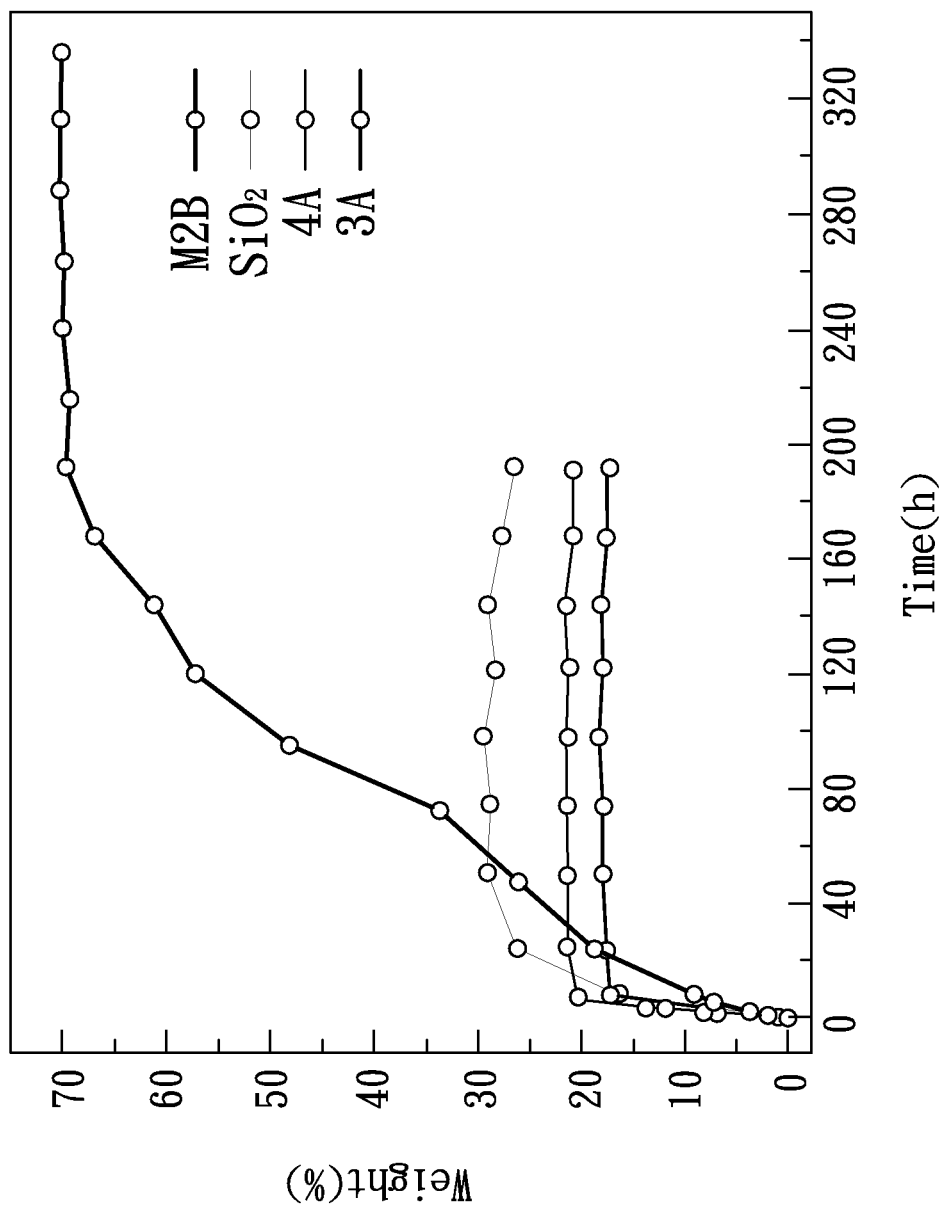
FIG. 7 shows dehumidifying capabilities of M2B and some commercial desiccants including silica gel and molecular sieves 3A and molecular sieves 4A.

FIG. 7 shows dehumidifying capabilities of M2B and some commercial desiccants including silica gel and molecular sieves 3A and molecular sieves 4A. All samples are pre-treated by heating in air for 5 hrs at 250° C. and then placed under an environment with a relative humidity about 70%. The more dehumidifying-capability the drying agent has, the more weight percentage the drying agent increase. The results show that M2B will be regenerated to compound 1, with a maximum of 90% (calculated 96.6%) weight increase, which indicates an amazingly high water sorption capacity. And the adsorption capacity of M2B is nearly double of the silica gel and triple of the molecular sieves 3A and 4A. The advantage of M2B is even more pronounced when the pre-treating temperature is higher.

Figure 8:
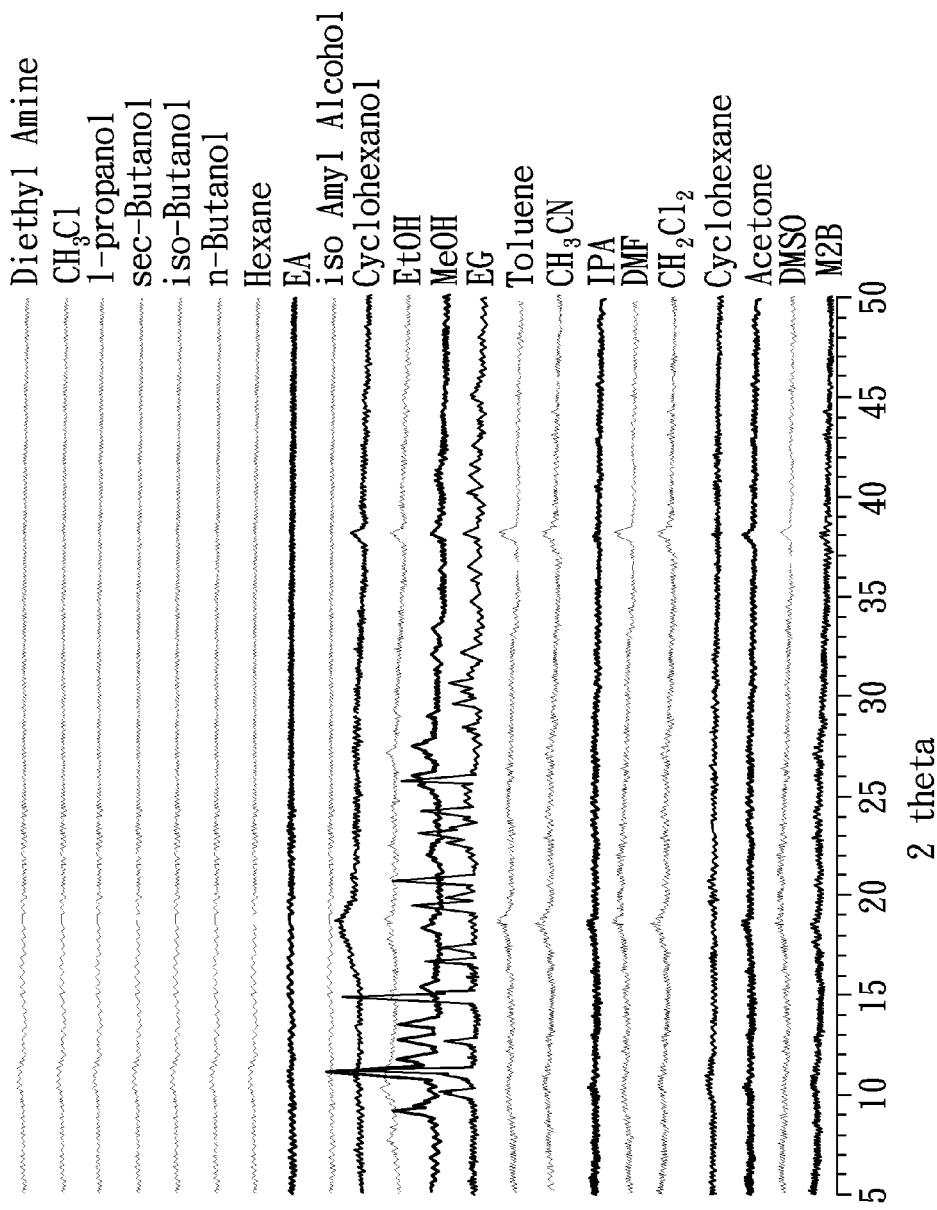
FIG. 8 shows XRD patterns of M2Bs placed in various organic solvents for one week to investigate the potential of M2B as drying agent for solvents.

FIG. 8 shows XRD patterns of M2Bs placed in various organic solvents for one week to investigate the potential of M2B as drying agent for solvents. The solvents includes diethyl amine, methyl chloride ($CH_3Cl$), 1-propanol, sec-butanol, iso-butanol, n-butanol, hexane, ethyl acetate (EA), iso amyl alcohol, cyclohexanol, ethyl alcohol (EtOH), methyl alcohol (MeOH), ethyl glycol, toluene, acetonitrile ($CH_3CN$), isopropyl alcohol (IPA), dimethyl fumarate (DMF), dichloromethane ($CH_2Cl_2$), cyclohexane, acetone, and dimethyl sulfoxide (DMSO). The results show that two additional crystalline species were found in the M2B samples immersed in methanol and ethylene glycol, and this mean that M2B is stable and insoluble in most of those solvents for one week.

It is appreciated that the described compound 1, compound 2, and M2B are primary and stable structures obtained by the methods of the embodiments of the present invention. All of them can function as a drying agent after pre-heating with a temperature below 500° C. For example, all of them can function as a drying agent or purifier of a chemical reagent, such as the above-mentioned organic solvents. In addition, by varying the process parameters, similar structures with different number of coordination water and lattice water can be obtained, that is, the embodiments of the present invention provide structure with the following formula: $[Mg_2(BTEC)(H_2O)m]\cdot nH_2O$, which the number of coordination water is m, and the number of lattice water is n, m denotes zero or positive integers from 1 to 10, and n denotes zero or positive integers from 1 to 6.

In addition, in the preferred embodiment the above-mentioned chemical reaction is carried out under room temperature and pressure for saving energies; however, in other embodiments, the chemical reaction can be carried out under other temperatures, pressures, and relative humidity. According to the chemical mechanism of the present invention, the above-mentioned chemical reaction can be proceed as long as liquid water or gaseous water is existed at the temperature and pressure of the reaction. In some embodiments, the temperature of the reaction may be controlled at about 15 to 40° C. to avoid the expense of too much energy for controlling the temperature.

In the methods provided by the present invention, all reactants react to form the product, no by-product and intermediate produced and no solvent needed, the manufacturing cost being quite low. Further, the produced compound 1, compound 2, M2B, and the likes are toxicity-free and non-corrosive, the manufacturing process will not generate any hazardous substances to harm the human being and environment in compliance with concepts of the Green Chemistry. Moreover, the produced drying agents may be used in various fields, for example used as a desiccating agent or a purifier of a chemical reagent, and the drying agents of the present invention are reusable and more effective than that of prior art.

Although specific embodiments have been illustrated and described, it will be appreciated by those skilled in the art that various modifications may be made without departing from the scope of the present invention, which is intended to be limited solely by the appended claims.

What is claimed is:

1. A drying agent with a formula:

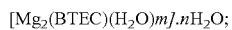
$[Mg_2(BTEC)(H_2O)m]\cdot nH_2O$;

wherein m denotes zero or positive integer from 1 to 10, and n denotes zero or positive integer from 1 to 6.

2. The drying agent as recited in claim 1, when both m and n are zero, the drying agent is thermally stable below a temperature about 500° C.

3. The drying agent as recited in claim 1, wherein the drying agent is employed to remove water from a chemical reagent.

4. The drying agent as recited in claim 3, wherein the chemical reagent comprises an organic solvent.

5. The drying agent as recited in claim 4, wherein the organic solvent comprises diethyl amine, methyl chloride ($CH_3Cl$), 1-propanol, sec-butanol, iso-butanol, n-butanol, hexane, ethyl acetate (EA), iso amyl alcohol, cyclohexanol, ethyl alcohol (EtOH), toluene, acetonitrile ($CH_3CN$), isopropyl alcohol (IPA), dimethyl fumarate (DMF), dichloromethane ($CH_2Cl_2$), cyclohexane, acetone, and dimethyl sulfoxide (DMSO).

6. The drying agent as recited in claim 1, wherein m is 10 and n is positive integer from 1 to 6.

* * * * *